(12) United States Patent
Wu et al.

(10) Patent No.: US 12,123,039 B2
(45) Date of Patent: Oct. 22, 2024

(54) PREPARATION OF THERMOPHILIC BETA-GLUCOSIDASE AND APPLICATION THEREOF

(71) Applicant: Jiangnan University, Wuxi (CN)

(72) Inventors: Jing Wu, Wuxi (CN); Wei Xia, Wuxi (CN); Xinghao Xu, Wuxi (CN); Yan Huang, Wuxi (CN)

(73) Assignee: Jiangnan University, Wuxi (CN)

( * ) Notice: Subject to any disclaimer, the term of this patent is extended or adjusted under 35 U.S.C. 154(b) by 477 days.

(21) Appl. No.: 17/520,811

(22) Filed: Nov. 8, 2021

(65) Prior Publication Data

US 2022/0056496 A1   Feb. 24, 2022

Related U.S. Application Data

(63) Continuation of application No. PCT/CN2020/102671, filed on Jul. 17, 2020.

(30) Foreign Application Priority Data

Apr. 27, 2020  (CN) .......................... 202010342426.0

(51) Int. Cl.
*C12P 19/14* (2006.01)
*C12N 9/42* (2006.01)

(52) U.S. Cl.
CPC ............ *C12P 19/14* (2013.01); *C12N 9/2445* (2013.01); *C12Y 302/01021* (2013.01)

(58) Field of Classification Search
CPC .. C12R 2001/84; C12N 15/815; C12N 15/03; C12N 15/09
See application file for complete search history.

(56) References Cited

FOREIGN PATENT DOCUMENTS

| CN | 101492661 A | 7/2009 |
| CN | 105238827 A | 1/2016 |
| CN | 107099565 A | 8/2017 |

OTHER PUBLICATIONS

He et al. 3 Biotech., 2017, 7, 368, 1-4 (Year: 2017).*
Liu,Iingling et. al., "Production of gentiooligosaccharide by recombinant-glucosidase" Acta Microbiologica Sinica, 49(5):597-602,May 4, 2009.
He R.L. et. al., "Genome sequence of Talaromyces piceus 9-3 provides insights into lignocellulose degradation", 3 Biotech, V7, Issue 368, Oct. 10, 2017.
E R.L. et. al., "Mutagenesis and evaluation of cellulase properties and cellulose hydrolysis of Talaromyces piceus", World J Microbiol Biotechnol, V31,Sep. 2, 2015.
He R. et. al., "beta-glucosidase [*Talaromyces piceae*]", GenBank: ATQ35964.1,Nov. 7, 2017.

* cited by examiner

*Primary Examiner* — Sharmila G Landau
*Assistant Examiner* — Lioubov G Korotchkina
(74) *Attorney, Agent, or Firm* — IPRO, PLLC

(57) ABSTRACT

The disclosure discloses the preparation of thermophilic β-glucosidase and the application thereof, which belongs to the technical field of genetic engineering and fermentation engineering. The present disclosure heterologously expresses the β-glucosidase TpBgl3A derived from thermophilic fungus *Talaromyces piceae* by constructing a recombinant bacteria. The enzyme production of recombinant bacteria can reach 2324 U/mL in a 3.6 L fermenter. The resulting β-glucosidase TpBgl3A can produce gentioligosaccharides with a high conversion rate using glucose as a substrate at a lower enzyme amount added, which significantly reduces production costs. In the reaction system using glucose and cellobiose as substrates, the conversion rate of gentioligosaccharide reaches 26.2%, which has the potential for industrial production of gentioligosaccharide.

8 Claims, 4 Drawing Sheets

Specification includes a Sequence Listing.

SEQUENCE LISTING

<160> NUMBER OF SEQ ID NOS: 3

<210> SEQ ID NO 1
<211> LENGTH: 2145
<212> TYPE: DNA
<213> ORGANISM: Artificial Sequence
<220> FEATURE:
<223> OTHER INFORMATION: Synthetic DNA

<400> SEQUENCE: 1

```
caaacttctg attgggatga agcttactct aaggctttgg attctttggc taagttgtct      60
caaaacgaaa agattggtat tgttactggt acttcttggc aaaacggttc ttgtgttggt     120
aacacttacc aaccatcttc tattgattac ccatctttgt gtttgcaaga tggtccattg     180
ggtattagat acgctaaccc agttactgct tttccagctg gtattaacgc tggtgctact     240
tgggatagat ctttgattaa ggatagaggt gctgctttgg gtgaagaagc taagtctttg     300
ggtgttcatg tttctttggg tccagttgct ggtccattgg gtaaggttcc acaaggtggt     360
agattgtggg aaggttttto tgttgatcca tacttgtctg gtgttgctat gactgaaact     420
attaacggtg ttcaaggtgc tggtgctcaa gcttgtgcta agcattacat tggtaacgaa     480
```

-continued

| | |
|---|---|
| caagaaacta acagaaacta cattgattct actattgatg atagagcttt tcatgaattg | 540 |
| tacttgtggc catttgctga tgctgttaga gctaacgttg cttctgttat gtgttcttac | 600 |
| aacaaggtta acggtactta cacttgtgaa aacccagctg ttttgaacca tactttgaag | 660 |
| actgaattgg ttttaaggg ttacattatg tctgattggg gtgctcaaca tactacttct | 720 |
| ggttctgcta acgctggttt ggatatgact atgccaggtt ctgatttgtc taacccacca | 780 |
| ggtaacgttt tgtggggtca aaagttggct gatgctattt ctaacggtga agttgaacaa | 840 |
| tctagattgg atgatatggt tactagaatt ttggctgctt ggtacttggt tggtcaagat | 900 |
| caaggttacc catctgttca atttaactct tggaacggtg tcaaacttc tgctaacgtt | 960 |
| actggtgatc atgctactgt tgttagaaac gttgctagag attctattgt tttgttgaag | 1020 |
| aacgataaca cacttttgcc attgtctaag ccaaactctt tggctattat tggttctgat | 1080 |
| gctgctgtta acccagatgg tccaaacgct tgttctgata gaggttgtga tactggtact | 1140 |
| ttggctatgg gttggggttc tggtacttgt gaatttccat acttggttgg tccattggaa | 1200 |
| gctattaaga accaagctaa cgctgatggt actactatta cttcttctac tactgattct | 1260 |
| acttctgatg gtgcttctgc tgctcaaaac gctgatgttg ctattgtttt tattaactct | 1320 |
| gattctggtg aaggttacat taacgttgaa ggttcttctg gtgatagatt gaacttggat | 1380 |
| ccatggcatt ctggtaacga attggttcaa gctgttgctc aagttaacca aaagactatt | 1440 |
| gttgttattc attctgttgg tccattggtt ttggaatcta ttttggctga accaaacgtt | 1500 |
| gttgctattg tttgggctgg tttgccaggt caagaatctg gtaacgcttt ggttgatatt | 1560 |
| ttgtacggtt ctactgctcc atctggtaag ttgccataca ctattgctaa gcaagaatct | 1620 |
| gattacggta cttctgttgt taacggtgat gataactttt ctgaaggtat ttttgttgat | 1680 |
| tacagacatt ttgatcatgc tgatattgaa ccaagatacg aatttggtta cggtttgtct | 1740 |
| tacactactt ttaactactc tggttttggct gttgatgtta ctgtttctgc tggtgctact | 1800 |
| tctggtgaaa ctgtttctgg tggtccatct gatttgttta ctgaagttgg tactgtttct | 1860 |
| gcttctgttc aaaacactgg tcaagttact ggtgctgaag ttgctcaatt gtacattggt | 1920 |
| ttgccatctt ctgctccatc tgctccacca aagcaattga gaggttttca aaagattttg | 1980 |
| ttggaagctg atgaatctga tactgcttct ttttctttga ctagaagaga tttgtcttac | 2040 |
| tgggatactc aagaacaaaa gtgggttgtt ccatctggtg aatttctgt ttacgttggt | 2100 |
| tcttcttcta gagatattag attgactgat acttttactg tttaa | 2145 |

<210> SEQ ID NO 2
<211> LENGTH: 714
<212> TYPE: PRT
<213> ORGANISM: Talaromyces piceae

<400> SEQUENCE: 2

Gln Thr Ser Asp Trp Asp Glu Ala Tyr Ser Lys Ala Leu Asp Ser Leu
1               5                   10                  15

Ala Lys Leu Ser Gln Asn Glu Lys Ile Gly Ile Val Thr Gly Thr Ser
            20                  25                  30

Trp Gln Asn Gly Ser Cys Val Gly Asn Thr Tyr Gln Pro Ser Ser Ile
        35                  40                  45

Asp Tyr Pro Ser Leu Cys Leu Gln Asp Gly Pro Leu Gly Ile Arg Tyr
    50                  55                  60

Ala Asn Pro Val Thr Ala Phe Pro Ala Gly Ile Asn Ala Gly Ala Thr
65                  70                  75                  80

```
Trp Asp Arg Ser Leu Ile Lys Asp Arg Gly Ala Ala Leu Gly Glu
                 85                  90                  95

Ala Lys Ser Leu Gly Val His Val Ser Leu Gly Pro Val Ala Gly Pro
            100                 105                 110

Leu Gly Lys Val Pro Gln Gly Gly Arg Leu Trp Glu Gly Phe Ser Val
            115                 120                 125

Asp Pro Tyr Leu Ser Gly Val Ala Met Thr Glu Thr Ile Asn Gly Val
130                 135                 140

Gln Gly Ala Gly Ala Gln Ala Cys Ala Lys His Tyr Ile Gly Asn Glu
145                 150                 155                 160

Gln Glu Thr Asn Arg Asn Tyr Ile Asp Ser Thr Ile Asp Asp Arg Ala
                165                 170                 175

Phe His Glu Leu Tyr Leu Trp Pro Phe Ala Asp Ala Val Arg Ala Asn
            180                 185                 190

Val Ala Ser Val Met Cys Ser Tyr Asn Lys Val Asn Gly Thr Tyr Thr
            195                 200                 205

Cys Glu Asn Pro Ala Val Leu Asn His Thr Leu Lys Thr Glu Leu Gly
            210                 215                 220

Phe Lys Gly Tyr Ile Met Ser Asp Trp Gly Ala Gln His Thr Thr Ser
225                 230                 235                 240

Gly Ser Ala Asn Ala Gly Leu Asp Met Thr Met Pro Gly Ser Asp Leu
                245                 250                 255

Ser Asn Pro Pro Gly Asn Val Leu Trp Gly Gln Lys Leu Ala Asp Ala
                260                 265                 270

Ile Ser Asn Gly Glu Val Glu Gln Ser Arg Leu Asp Asp Met Val Thr
        275                 280                 285

Arg Ile Leu Ala Ala Trp Tyr Leu Val Gly Gln Asp Gln Gly Tyr Pro
290                 295                 300

Ser Val Gln Phe Asn Ser Trp Asn Gly Gly Gln Thr Ser Ala Asn Val
305                 310                 315                 320

Thr Gly Asp His Ala Thr Val Val Arg Asn Val Ala Arg Asp Ser Ile
                325                 330                 335

Val Leu Leu Lys Asn Asp Asn Asn Thr Leu Pro Leu Ser Lys Pro Asn
            340                 345                 350

Ser Leu Ala Ile Ile Gly Ser Asp Ala Ala Val Asn Pro Asp Gly Pro
            355                 360                 365

Asn Ala Cys Ser Asp Arg Gly Cys Asp Thr Gly Thr Leu Ala Met Gly
370                 375                 380

Trp Gly Ser Gly Thr Cys Glu Phe Pro Tyr Leu Val Gly Pro Leu Glu
385                 390                 395                 400

Ala Ile Lys Asn Gln Ala Asn Ala Asp Gly Thr Thr Ile Thr Ser Ser
                405                 410                 415

Thr Thr Asp Ser Thr Ser Asp Gly Ala Ser Ala Ala Gln Asn Ala Asp
            420                 425                 430

Val Ala Ile Val Phe Ile Asn Ser Asp Ser Gly Glu Gly Tyr Ile Asn
            435                 440                 445

Val Glu Gly Ser Ser Gly Asp Arg Leu Asn Leu Asp Pro Trp His Ser
    450                 455                 460

Gly Asn Glu Leu Val Gln Ala Val Ala Gln Val Asn Gln Lys Thr Ile
465                 470                 475                 480

Val Val Ile His Ser Val Gly Pro Leu Val Leu Glu Ser Ile Leu Ala
                485                 490                 495
```

```
Glu Pro Asn Val Val Ala Ile Val Trp Ala Gly Leu Pro Gly Gln Glu
                500                 505                 510

Ser Gly Asn Ala Leu Val Asp Ile Leu Tyr Gly Ser Thr Ala Pro Ser
        515                 520                 525

Gly Lys Leu Pro Tyr Thr Ile Ala Lys Gln Glu Ser Asp Tyr Gly Thr
    530                 535                 540

Ser Val Val Asn Gly Asp Asn Phe Ser Glu Gly Ile Phe Val Asp
545                 550                 555                 560

Tyr Arg His Phe Asp His Ala Asp Ile Glu Pro Arg Tyr Glu Phe Gly
                565                 570                 575

Tyr Gly Leu Ser Tyr Thr Thr Phe Asn Tyr Ser Gly Leu Ala Val Asp
            580                 585                 590

Val Thr Val Ser Ala Gly Ala Thr Ser Gly Glu Thr Val Ser Gly Gly
        595                 600                 605

Pro Ser Asp Leu Phe Thr Glu Val Gly Thr Val Ser Ala Ser Val Gln
    610                 615                 620

Asn Thr Gly Gln Val Thr Gly Ala Glu Val Ala Gln Leu Tyr Ile Gly
625                 630                 635                 640

Leu Pro Ser Ser Ala Pro Ser Ala Pro Pro Lys Gln Leu Arg Gly Phe
                645                 650                 655

Gln Lys Ile Leu Leu Glu Ala Asp Glu Ser Asp Thr Ala Ser Phe Ser
            660                 665                 670

Leu Thr Arg Arg Asp Leu Ser Tyr Trp Asp Thr Gln Glu Gln Lys Trp
        675                 680                 685

Val Val Pro Ser Gly Glu Phe Ser Val Tyr Val Gly Ser Ser Ser Arg
    690                 695                 700

Asp Ile Arg Leu Thr Asp Thr Phe Thr Val
705                 710

<210> SEQ ID NO 3
<211> LENGTH: 740
<212> TYPE: PRT
<213> ORGANISM: Talaromyces piceae

<400> SEQUENCE: 3

Met Leu Ser Lys Leu Gln His Leu Val Ala Pro Ser Ile Leu Leu Ser
1               5                   10                  15

Leu Phe Ala Val Ser Lys Thr Thr Ser Ala Gln Thr Ser Asp Trp Asp
                20                  25                  30

Glu Ala Tyr Ser Lys Ala Leu Asp Ser Leu Ala Lys Leu Ser Gln Asn
            35                  40                  45

Glu Lys Ile Gly Ile Val Thr Gly Thr Ser Trp Gln Asn Gly Ser Cys
    50                  55                  60

Val Gly Asn Thr Tyr Gln Pro Ser Ser Ile Asp Tyr Pro Ser Leu Cys
65                  70                  75                  80

Leu Gln Asp Gly Pro Leu Gly Ile Arg Tyr Ala Asn Pro Val Thr Ala
                85                  90                  95

Phe Pro Ala Gly Ile Asn Ala Gly Ala Thr Trp Asp Arg Ser Leu Ile
            100                 105                 110

Lys Asp Arg Gly Ala Ala Leu Gly Glu Glu Ala Lys Ser Leu Gly Val
    115                 120                 125

His Val Ser Leu Gly Pro Val Ala Gly Pro Leu Gly Lys Val Pro Gln
130                 135                 140

Gly Gly Arg Leu Trp Glu Gly Phe Ser Val Asp Pro Tyr Leu Ser Gly
145                 150                 155                 160
```

```
Val Ala Met Thr Glu Thr Ile Asn Gly Val Gln Gly Ala Gly Ala Gln
                165                 170                 175

Ala Cys Ala Lys His Tyr Ile Gly Asn Glu Gln Glu Thr Asn Arg Asn
                180                 185                 190

Tyr Ile Asp Ser Thr Ile Asp Asp Arg Ala Phe His Glu Leu Tyr Leu
                195                 200                 205

Trp Pro Phe Ala Asp Ala Val Arg Ala Asn Val Ala Ser Val Met Cys
            210                 215                 220

Ser Tyr Asn Lys Val Asn Gly Thr Tyr Thr Cys Glu Asn Pro Ala Val
225                 230                 235                 240

Leu Asn His Thr Leu Lys Thr Glu Leu Gly Phe Lys Gly Tyr Ile Met
                245                 250                 255

Ser Asp Trp Gly Ala Gln His Thr Thr Ser Gly Ser Ala Asn Ala Gly
                260                 265                 270

Leu Asp Met Thr Met Pro Gly Ser Asp Leu Ser Asn Pro Pro Gly Asn
                275                 280                 285

Val Leu Trp Gly Gln Lys Leu Ala Asp Ala Ile Ser Asn Gly Glu Val
            290                 295                 300

Glu Gln Ser Arg Leu Asp Asp Met Val Thr Arg Ile Leu Ala Ala Trp
305                 310                 315                 320

Tyr Leu Val Gly Gln Asp Gln Gly Tyr Pro Ser Val Gln Phe Asn Ser
                325                 330                 335

Trp Asn Gly Gly Gln Thr Ser Ala Asn Val Thr Gly Asp His Ala Thr
                340                 345                 350

Val Val Arg Asn Val Ala Arg Asp Ser Ile Val Leu Leu Lys Asn Asp
                355                 360                 365

Asn Asn Thr Leu Pro Leu Ser Lys Pro Asn Ser Leu Ala Ile Ile Gly
                370                 375                 380

Ser Asp Ala Ala Val Asn Pro Asp Gly Pro Asn Ala Cys Ser Asp Arg
385                 390                 395                 400

Gly Cys Asp Thr Gly Thr Leu Ala Met Gly Trp Gly Ser Gly Thr Cys
                405                 410                 415

Glu Phe Pro Tyr Leu Val Gly Pro Leu Glu Ala Ile Lys Asn Gln Ala
                420                 425                 430

Asn Ala Asp Gly Thr Thr Ile Thr Ser Ser Thr Thr Asp Ser Thr Ser
                435                 440                 445

Asp Gly Ala Ser Ala Ala Gln Asn Ala Asp Val Ala Ile Val Phe Ile
            450                 455                 460

Asn Ser Asp Ser Gly Glu Gly Tyr Ile Asn Val Glu Gly Ser Ser Gly
465                 470                 475                 480

Asp Arg Leu Asn Leu Asp Pro Trp His Ser Gly Asn Glu Leu Val Gln
                485                 490                 495

Ala Val Ala Gln Val Asn Gln Lys Thr Ile Val Ile His Ser Val
            500                 505                 510

Gly Pro Leu Val Leu Glu Ser Ile Leu Ala Glu Pro Asn Val Val Ala
                515                 520                 525

Ile Val Trp Ala Gly Leu Pro Gly Gln Glu Ser Gly Asn Ala Leu Val
                530                 535                 540

Asp Ile Leu Tyr Gly Ser Thr Ala Pro Ser Gly Lys Leu Pro Tyr Thr
545                 550                 555                 560

Ile Ala Lys Gln Glu Ser Asp Tyr Gly Thr Ser Val Val Asn Gly Asp
                565                 570                 575
```

-continued

```
Asp Asn Phe Ser Glu Gly Ile Phe Val Asp Tyr Arg His Phe Asp His
            580             585                 590

Ala Asp Ile Glu Pro Arg Tyr Glu Phe Gly Tyr Gly Leu Ser Tyr Thr
        595             600             605

Thr Phe Asn Tyr Ser Gly Leu Ala Val Asp Val Thr Val Ser Ala Gly
        610             615             620

Ala Thr Ser Gly Glu Thr Val Ser Gly Gly Pro Ser Asp Leu Phe Thr
625             630             635                     640

Glu Val Gly Thr Val Ser Ala Ser Val Gln Asn Thr Gly Gln Val Thr
                645             650             655

Gly Ala Glu Val Ala Gln Leu Tyr Ile Gly Leu Pro Ser Ser Ala Pro
            660             665             670

Ser Ala Pro Pro Lys Gln Leu Arg Gly Phe Gln Lys Ile Leu Leu Glu
        675             680             685

Ala Asp Glu Ser Asp Thr Ala Ser Phe Ser Leu Thr Arg Arg Asp Leu
        690             695             700

Ser Tyr Trp Asp Thr Gln Glu Gln Lys Trp Val Val Pro Ser Gly Glu
705             710             715                     720

Phe Ser Val Tyr Val Gly Ser Ser Ser Arg Asp Ile Arg Leu Thr Asp
                725             730             735

Thr Phe Thr Val
            740
```

PREPARATION OF THERMOPHILIC BETA-GLUCOSIDASE AND APPLICATION THEREOF

TECHNICAL FIELD

The disclosure relates to the preparation of thermophilic β-glucosidase and the application thereof, and belongs to the technical field of genetic engineering and fermentation engineering.

BACKGROUND

Gentioligosaccharide is a new functional oligosaccharide formed by the combination of glucose via β-1,6 glycosidic bonds. Gentioligosaccharides include gentiobiose and a small amount of gentiotrioses and gentiotetraoses. Gentioligosaccharide is not degraded by human enzymes and has low calories, which is suitable for consumption by people with obesity, hyperlipidemia, hypertension, diabetes, etc. It also has high moisture retention and hygroscopicity, which is beneficial to maintain water in food, and can prevent the aging of starchy foods. At the same time, gentioligosaccharide has high pH and thermal stability, which is suitable for food used under high temperature and special pH conditions. It has low water activity, which can effectively prevent food from being contaminated by microorganisms. It also has a soft refreshing bitterness, which can be added to food to increase the richness of flavor. At present, gentioligosaccharides are widely used in chocolate, ice cream, coffee, condiments, baked foods and beverages.

Gentioligosaccharides were first extracted from the rhizomes of Gentian plants or obtained by hydrolyzing starch with sulfuric acid. The yield of these two methods is extremely low and the product has complicated ingredients difficult to separate and extract. Although chemical synthesis having high yields is currently used in most of the industry, this method is easy to result in environmental pollution. Therefore, enzymatic production has become a trend at present. The current research mainly focuses on forming a product by polymerizing glucose as a substrate through transglycosylation using β-glucosidase. β-glucosidase is distributed in 6 families of glycoside hydrolase (GH) such as 1, 3, 5, 9, 30 and 116, and it is widely present in plants, animals and microorganisms. Among them, the microorganism source is more extensive.

SUMMARY

β-glucosidase can hydrolyze and release the glucose group at the non-reducing end of β-D-glycoside compounds. It is an important member of the cellulose-degrading enzyme system and can prevent the accumulation of cellobiose during the process of cellulose degradation, thereby effectively relieving the strong product inhibition of cellobiose on upstream endo-cellulase and exo-cellulase.

The present disclosure provides a gene sequence encoding the mature protein of β-glucosidase TpBgl3A, and the nucleotide sequence of the gene is as set forth in SEQ ID NO:1.

In one example, the β-glucosidase is the mature protein of β-glucosidase TpBgl3A, and its amino acid sequence is as set forth in SEQ ID NO:2.

The present disclosure provides a vector carrying a gene with nucleotide sequence as set forth in SEQ ID NO:1.

In one example, the expression vector of the vector is pPIC9K.

The present disclosure provides a recombinant bacteria carrying a gene with nucleotide sequence as set forth in SEQ ID NO:1.

In one example, the recombinant bacteria expresses the mature protein of β-glucosidase TpBgl3A with amino acid sequence as set forth in SEQ ID NO:2 with *Pichia pastoris* KM71 as a host.

The present disclosure provides a method for producing β-glucosidase, including subjecting the recombinant bacteria carrying a gene with nucleotide sequence as set forth in SEQ ID NO:1 to high-density fermentation to produce the β-glucosidase.

In one example, the recombinant bacteria expresses β-glucosidase with amino acid sequence as set forth in SEQ ID NO:2 with pPIC9K as an expression vector and *Pichia pastoris* KM71 as a host.

In one example, a single colony of recombinant bacteria is picked into YPD medium, cultivated at 30° C. for 36 h to obtain a seed liquid, and the seed liquid is inoculated into the fermentor at a volume ratio of 8% to 12%, the temperature is controlled at 28-30° C., the initial rotation speed is controlled at 180-220 rpm, the initial ventilation quantity is controlled at 5-8 L/min, the dissolved oxygen concentration is controlled at 28-32% and pH is controlled at 4.5-5.5; when the dissolved oxygen concentration increases to 80-100%, a fed-batch culture is performed by constantly feeding glycerol; when the cell concentration of recombinant bacteria is an $OD_{600}$ of 100-150, 1-1.5 mL/100 mL methanol is used to induce the enzyme production by recombinant bacteria, the temperature is controlled at 20-25° C., the dissolved oxygen concentration is controlled at 28-32%, and pH is controlled at 4.5-5.5.

In one example, the concentration of glycerol is 80% (v/v), and the feeding rate of glycerol is 15-25 mL/h.

In one example, the concentration of methanol is 1 mL/100 mL, and the induction time is not less than 120 h.

In one example, the high-density fermentation conditions are: when the cell concentration of recombinant bacterial is an $OD_{600}$ of 150, methanol at a concentration of 1 mL/100 mL is added to induce enzyme production, the temperature is controlled at 25° C., and the fermentation time is not less than 144 h.

The present disclosure provides a method for producing gentioligosaccharide including producing gentioligosaccharide with glucose or a combination of glucose and cellobiose as a substrate using β-glucosidase expressed by recombinant bacteria carrying a gene with nucleotide sequence as set forth in SEQ ID NO:1.

In one example, the amino acid sequence of the β-glucosidase is as set forth in SEQ ID NO:2.

In one example, when glucose is used as the substrate, the concentration of glucose is 800 g/L.

In one example, the enzyme amount of β-glucosidase added is 200-300 U/g glucose.

In one example, the reaction is carried out at pH 5.0 and 60° C. for not less than 72 h.

In one example, when a combination of glucose and cellobiose is used as the substrate, the concentration of glucose is 75 g/L and the concentration of cellobiose is 300 g/L; alternatively, the concentration of glucose is 100 g/L and the concentration of cellobiose is 400 g/L.

In one example, the enzyme amount of the β-glucosidase added is 400 U/g cellobiose.

In one example, the reaction is carried out at pH 5.0 and 60° C. for 48 h.

The present disclosure claims the application of the gene encoding β-glucosidase TpBgl3A with nucleotide sequence as set forth in SEQ ID NO:1 in the preparation of gentioligosaccharides in the fields of food and cosmetics.

The disclosure claims the application of the recombinant bacteria carrying the gene with nucleotide sequence as set forth in SEQ ID NO:1 in the preparation of gentioligosaccharides in the field of food and cosmetics.

The disclosure claims the application of the vector in the preparation of gentioligosaccharides in the fields of food and cosmetics.

The disclosure claims the application of the method for producing β-glucosidase in the preparation of gentioligosaccharides in the fields of food and cosmetics.

The present disclosure also claims the application of the method for producing gentioligosaccharides in the preparation of oligogentianose in the field of food and cosmetics.

The beneficial effects of the present disclosure: the present disclosure obtains a genetically engineered strain KM71/pPIC9K-TpBgl3A for high β-glucosidase production by heterologously expressing the β-glucosidase derived from *Talaromyces piceae* into *Pichia pastoris* with pPIC9K as the expression vector and *Pichia pastoris* KM71 as the expression host. The enzyme production of genetically engineered bacteria KM71/pPIC9K-TpBgl3A can reach 2324 U/mL in a 3.6 L fermenter. For the produced β-glucosidase TpBgl3A, the enzyme amount added is lower, the substrate conversion rate and the yield of gentioligosaccharides are higher, compared to other similar enzymes in existing production. When the enzyme amount added is 300 U/g, the highest yield of gentioligosaccharides can reach 125.0 g/L, the conversion rate is 15.62%, which has a good industrial value.

DETAILED DESCRIPTION

Figure 1:
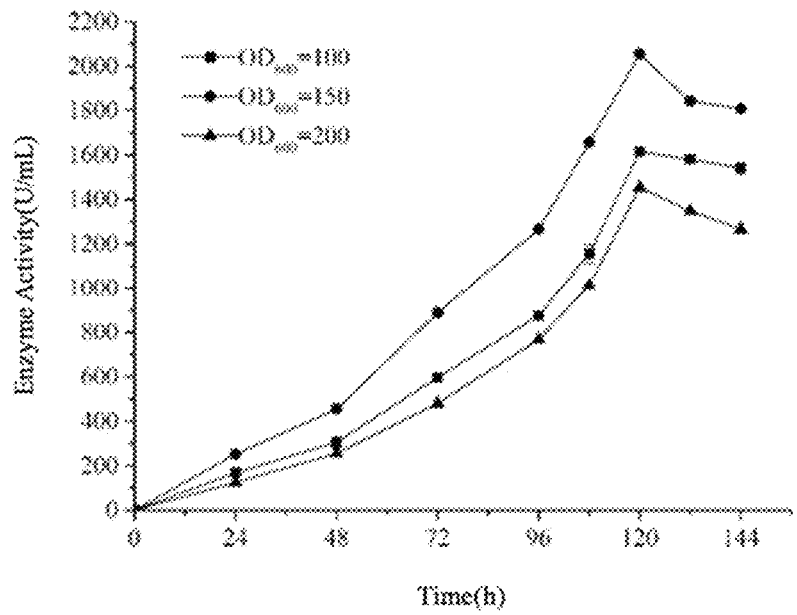
FIG. 1 is a diagram showing the relationship between the initial cell concentration for induction and the fermentation enzyme activity of the recombinant engineered bacteria KM71-pPIC9K-TpBgl3A.

The medium required in the examples:
MD solid medium: YNB 13.4 g/L, biotin $4.0 \times 10^{-4}$ g/L, glucose 20 g/L, and agar 20 g/L.

YPD medium: peptone 20 g/L, yeast extract 10 g/L, and glucose 20 g/L; agar 20 g/L is added if a solid medium is desired.

BMGY medium: YNB 13.4 g/L, glycerol 10 g/L, biotin $4 \times 10^{-4}$ g/L, 0.1 mol/L potassium phosphate buffer (pH 6.0), peptone 20 g/L, and yeast powder 10 g/L.

Fermentation seed medium: yeast powder 5.0 g/L, tryptone 10.0 g/L, glucose 10.0 g/L, and glycerol 30 g/L.

BSM medium: 85% phosphoric acid 26.7 mL/L, $CaSO_4$ 0.93 g/L, $K_2SO_4$ 18.2 g/L, $MgSO_4 \cdot 7H_2O$ 14.9 g/L, KOH 4.13 g/L, glycerol 30.0 g/L, and trace element salt solution 4.32 mL/L.

Fed-batch medium for growth phase: 80% glycerol and 4.92 mL/L trace element solution.

Fed-batch medium for induction phase: 100% methanol, 12.5 mL/L trace element solution; 100% ammonia and 50% phosphoric acid are used to adjust pH for high-density fermentation.

Analysis of β-glucosidase enzyme activity:
(1) Definition of Enzyme Activity Unit One unit of enzyme activity refers to the enzyme activity of producing 1 μmol of p-nitrophenol by hydrolyzing pNPG with 1 milliliter of enzyme solution per minute.

(2) Steps for Determining Enzyme Activity

The reaction system is 1 mL, where 960 μl of acetic acid buffer at pH 5.0 is added, 20 μl of appropriately diluted crude enzyme solution is added, and then 20 μl of 100 mmol/L pNPG is added, the reaction is carried out in a constant temperature water bath at 60° C. for 10 min, and then 200 μl of 1 mol/L $Na_2CO_3$ solution is immediately added to stop the reaction. The mixture is cultured in an ice bath for 5 min, and the absorbance is measured at 405 nm. The heat-inactivated enzyme solution is treated in the same way and used as a blank.

The recovery kit was purchased from Tiangen Biotech Co., Ltd.

Example 1: Construction of Genetically Engineered Bacteria KM71/pPIC9K-TpBgl3A by *Pichia pastoris*

According to the amino acid sequence of β-glucosidase derived from *Talaromyces piceae* in the database (NCBI accession number ATQ35964, the amino acid sequence is as set forth in SEQ ID NO:3), the coding sequence for mature protein of β-glucosidase TpBgl3A (with the signal peptide sequence removed) (nucleotide sequence is as set forth in SEQ ID NO:1) was chemically synthesized.

After that, the coding sequence of TpBgl3A was inserted into the downstream region of α-factor signal peptide (including the initiation codon atg) of the yeast expression vector pPIC9K for fusion expression. The specific method was: the coding sequence of TpBgl3A and the vector pPIC9K were respectively digested with EcoR I and Not I restriction enzymes, recovered and then ligated with T4 ligase to obtain a ligation product, the ligation product was transferred into *E.coli*.JM109 to obtain a transformation product; the transformation product was spread on a LB solid medium containing 0.05 mg/mL Kanamycin and cultured inverted in a constant temperature incubator at 37° C. for 8-12 h to obtain transformants.

Heat-Shock transformation method:
(1) *E.coli*.JM109 competent cells were placed on ice for 5 min in advance, after the competent cells were completely thawed, 10 µl of complete plasmid or PCR product was added, gently pipetted, mixed well, and then placed on ice for 45 min;
(2) the competent cells were placed in a water bath at 42° C. for heat-shock for 90 s, and then placed on ice for 5 min;
(3) after the incubation in an ice bath was over, 0.8 mL of LB liquid medium was added to the competent cells, mixed well, and then placed in a shaker at 37° C. and cultured with shaking for about 60 min; and
(4) after the culture was over, the competent cells were centrifuged at 3000 rpm for 5 min, part of the supernatant was discarded, about 200 µl of fermentation broth was retained, the bacterial cells were re-pipetted and re-suspended, spread on a LB solid plate containing ampicillin, static cultured in an incubator at 37° C. for about 10 h and then a single colony was grown on the plate.

A single colony was picked and inoculated into a LB liquid medium containing 0.05 mg/mL kanamycin, cultured with shaking at 37° C. and 120-180 rpm for 8-12 h, then the plasmid was extracted for enzyme digestion verification and sequencing verification, and a recombinant plasmid pPIC9K-TpBgl3A was obtained as verification was correct.

The recombinant plasmid pPIC9K-TpBgl3A was integrated into *Pichia pastoris* KM71 by electrotransformation.

The preparation and transformation steps of *Pichia pastoris* KM71 competent cells were as follows:
(1) 30 µl of bacterial solution was pipetted from the *Pichia pastoris* KM71 glycerol tube and inoculated into 10 mL of YPD liquid medium, cultured in a 30° C. shaker at 200 rpm for 24 h, and then from which 100 µl was pipetted and inoculated into 100 mL of YPD liquid medium, and cultured with shaking at constant temperature of 30° C. for 16 h;
(2) under a sterile environment, the bacterial solution was dispensed into three pre-cooled 50 mL centrifuge tubes, centrifuged at 5000 rpm for 5 min at 4° C., and then the supernatant was discarded and the bacterial cells were collected;
(3) under a sterile environment, the bacterial cells were re-suspended with 4 mL ddH$_2$O, then combined into one tube, and 2 mL TE buffer, 2 mL LiAc buffer and 0.5 mL DTT buffer were added successively, gently pipetted and mixed well, the centrifuge tube was placed in a 30° C. water bath shaker at 50 rpm and cultured for 45-50 min, where all the above reagents shall be treated by pre-cooling;
(4) under a sterile environment, 13.5 mL of pre-cooled ddH$_2$O was added to the centrifuge tube, centrifuged at 5000 rpm for 5 min at 4° C., and then the supernatant was discarded and the bacterial cells were collected;
(5) under a sterile environment, the bacterial cells were re-suspended with 25 mL ddH$_2$O, centrifuged at 5000 rpm for 5 min at 4° C., and then the supernatant was discarded and the bacterial cells were collected, after that, the operation of resuspension and collection of bacterial cells was repeated twice with 25 mL of 1 M sorbitol;
(6) 1 mL of pre-cooled sorbitol was added to the centrifuge tube, the bacterial cells were gently re-suspended, dispensed into 1.5 mL EP tubes at a rate of 80 µl per tube and temporarily stored in a low-temperature refrigerator at −80° C.;
(7) 10 µl of linearized plasmid was added to the *Pichia pastoris* KM71 competent cells and mixed well by gently tapping the tube wall, then the competent cells were added along the wall to the pre-cooled electric shock cup, and air bubbles were eliminated by gently tapping the bottom of the electric shock cup;
(8) the electric shock cup was placed into an electroporator with a voltage of 1500 V for electric shock;
(9) the electric shock cup was taken out immediately, the pre-cooled 1 mL of 1 M sorbitol was quickly added, gently pipetted, mixed well, and then the bacterial solution was transferred to the EP tube, and incubated in a shaker at 30° C. for 1-2 h; and
(10) 100 µl of bacterial solution was pipetted from the EP tube, spread on the MD solid medium evenly, and cultured at 30° C. for 48 h.

Screening of transformants: After a single colony was grown on the above-mentioned MD plate, 96 transformants are picked with a sterilized toothpick and transferred to a numbered 10 mL culture tube containing 4 mL BMGY medium and a new MD plate according to the number at the same time. The MD plate was placed upside down in a constant temperature incubator at 30° C. and cultured. The culture tube was cultured with shaking at 30° C. and 220 rpm for 2 d and then centrifuged at 4,500 rpm for 5 min. The supernatant was discarded. The bacterial cells were re-suspended with a 2 mL BMGY medium for induction culture at 30° C. and 220 rpm for 2 d and then centrifuged to obtain the supernatant as the crude enzyme solution.

The supernatant was tested for β-glucosidase activity, and the recombinant transformant with the highest enzyme activity was screened out. The correspondingly numbered transformant plaque was picked from the corresponding MD plate, inoculated in an YPD medium for activated culture at 30° C. and 220 rpm for 2 d, and stored as the recombinant strain *Pichia pastoris*/KM71-pPIC9K-TpBgl3A.

Example 2: Enzyme Production by Recombinant *Pichia pastoris* Engineered Bacteria *Pichia pastoris*/KM71-pPIC9K-TpBgl3A 1. Fermentation of the Engineered Bacteria in a 3.6 L Fermenter
(1) Batch fermentation stage: the seed liquid (obtained by culturing the recombinant strain in YPD liquid medium at 30° C. for 36 h) was inoculated into the fermenter at an inoculum size of 8%-12% (v/v), the temperature was controlled at 28-30° C., the initial rotation speed was controlled at 180-220 rpm, the initial ventilation quantity was controlled at 7 L/min, the dissolved oxygen concentration was controlled at 28-32% and pH was controlled at 4.5-5.5;
(2) Feed-batch fermentation stage: when the dissolved oxygen concentration increased to 80-100%, a fed-batch culture was performed by constantly feeding glycerol, the temperature was controlled at 28-30° C., the dissolved oxygen concentration was controlled at 28-32% and pH was controlled at 4.5-5.5; the concentration of glycerol was 80% (v/v), and the feeding rate of glycerol is 17.5-18.5 mL/h; and
(3) Induction culture stage: when the concentration of bacterial cells was within the range of $OD_{600}$=100-200, methanol was fed with a methanol feeding equipment to induce enzyme production. The methanol concentration was controlled at 0.5%-1.5%, the temperature was controlled at 20-30° C., the dissolved oxygen concentration was controlled at 28-32% and pH was controlled at 4.5-5.5. After induction for 96-144 h, the fermentation was completed. The fermentation broth was centrifuged to obtain the supernatant as the crude enzyme solution.

2. Optimization of Fermentation Conditions

In order to increase the fermentation level of β-glucosidase, the $OD_{600}$ of the initial induced cell in the above step (3) was set to 100, 150, or 200, the methanol concentration was set to 0.5%, 1.0%, or 1.5% based on the medium volume, and the induction temperature was set to 20° C., 25° C., or 30° C. The influence of different fermentation conditions on the expression of recombinase was explored.

The specific optimization process is as follows:

(1) Cell concentration for initial induction: after feeding glycerol at a rate of 17.5-18.5 mL/h to allow the cell concentration reach the cell concentration for initial induction with different set values ($OD_{600}$=100, 150, 200, respectively), methanol was added to carry out the induction culture. The methanol concentration for induction was 1.0%, the temperature for induction culture was set to 25° C., and the fermentation process was completed after induction for 144 h. The results showed that the optimal cell concentration for initial induction was $OD_{600=150}$, and the highest enzyme activity of β-glucosidase produced by engineered bacteria reached 2054 U/mL (FIG. 1).

TABLE 1

Enzyme production (U/ml) of engineered bacteria at different cell concentrations for initial induction

|  | 24 h | 48 h | 72 h | 96 h | 120 h | 144 h |
| --- | --- | --- | --- | --- | --- | --- |
| $OD_{600}$ = 100 | 168 | 306 | 597 | 876 | 1615 | 1542 |
| $OD_{600}$ = 150 | 252 | 455 | 888 | 1267 | 2054 | 1808 |
| $OD_{600}$ = 200 | 124 | 255 | 481 | 767 | 1454 | 1267 |

Figure 2:
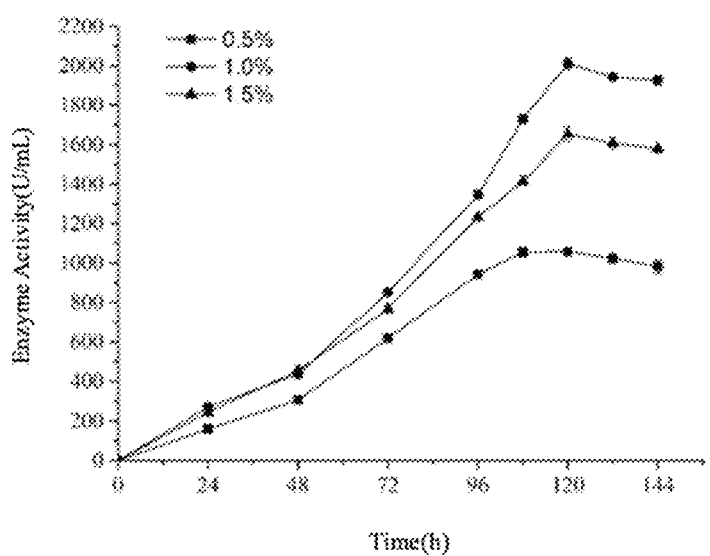
FIG. 2 is a diagram showing the relationship between the methanol concentration for induction and the fermentation enzyme activity of the recombinant engineered bacteria KM71-pPIC9K-TpBgl3A.

(2) Methanol concentration for induction: under the condition of initial cell concentration of $OD_{600}$=150 and the temperature for induction culture of 25° C., three different concentration gradients of methanol (0.5%, 1.0%, and 1.5% based on the medium volume) were used for induction, respectively, and the fermentation process was completed after induction for 144 h. The results showed that the optimal methanol concentration for induction was 1.0%, and the highest enzyme activity of β-glucosidase produced by recombinant bacteria reached 2010 U/mL (FIG. 2).

TABLE 2

Enzyme production (U/ml) of engineered bacteria induced by different concentrations of methanol

|  | 24 h | 48 h | 72 h | 96 h | 120 h | 144 h |
| --- | --- | --- | --- | --- | --- | --- |
| 0.5% methanol | 159 | 306 | 619 | 943 | 1058 | 982 |
| 1.0% methanol | 270 | 437 | 853 | 1346 | 2010 | 1926 |
| 1.5% methanol | 244 | 455 | 767 | 1232 | 1654 | 1579 |

Figure 3:
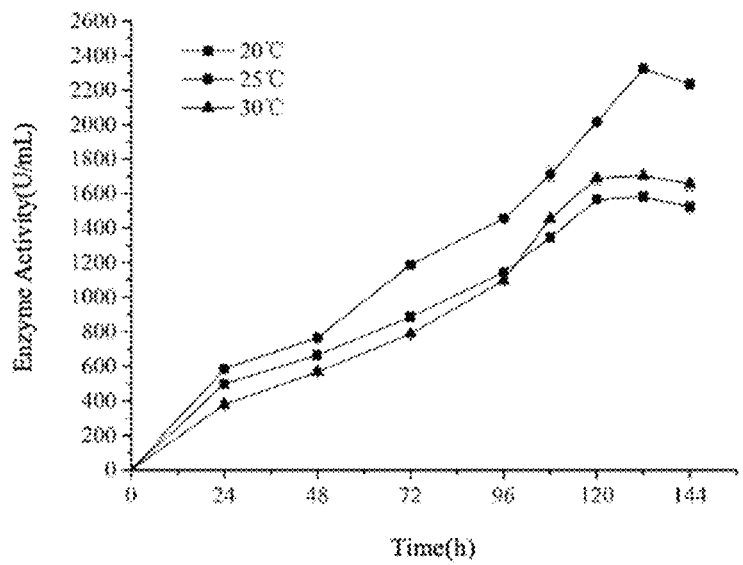
FIG. 3 is a diagram showing the relationship between the culture temperature for induction and the fermentation enzyme activity of the recombinant engineered bacteria KM71-pPIC9K-TpBgl3A.

(3) Temperature for induction culture: under the condition of the initial cell concentration of $OD_{600}$=150 and the methanol concentration for induction of 1.0%, the fermentation process was completed by respectively inducing at 3 culture temperatures of 20° C., 25° C., and 30° C. for 144 h. The results showed that the optimal temperature for induction culture was 25° C., and the highest enzyme activity of β-glucosidase produced by engineered bacteria reached 2324 U/mL (FIG. 3).

TABLE 3

Enzyme production (U/mL) of engineered bacteria at different temperatures for the induction culture

|  | 24 h | 48 h | 72 h | 96 h | 120 h | 144 h |
| --- | --- | --- | --- | --- | --- | --- |
| 20° C. | 498 | 665 | 886 | 1145 | 1565 | 1523 |
| 25° C. | 585 | 765 | 1188 | 1456 | 2015 | 2324 |
| 30° C. | 378 | 567 | 789 | 1096 | 1689 | 1657 |

Figure 4:
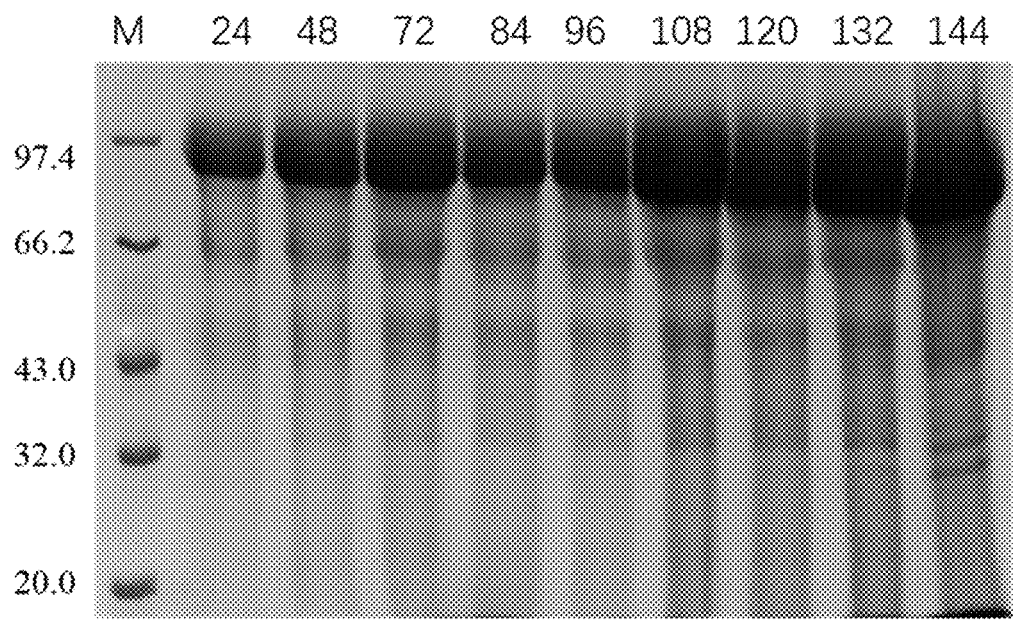
FIG. 4 is an SDS-PAGE electrophoresis diagram of the fermentation supernatant of recombinant bacteria in a 3.6 L fermentor; 24, 48, 72, 84, 96, 108, 120, 132, and 144 in the figure indicate that the fermentation time of 24 h, 48 h, 72 h, 84 h, 96 h, 108 h, 120 h, 132 h, and 144 h, respectively.

After optimization of fermentation conditions, under the optimal fermentation conditions where the cell concentration for initial induction was $OD_{600}$=150, the methanol concentration for induction was 1.0%, and the induction temperature was 25° C., the highest enzyme activity of β-glucosidase is measured to be 2324 U/mL. The SDS-PAGE electrophoresis diagram of the fermentation broth for the recombinant β-glucosidase is shown in FIG. 4.

Figure 5:
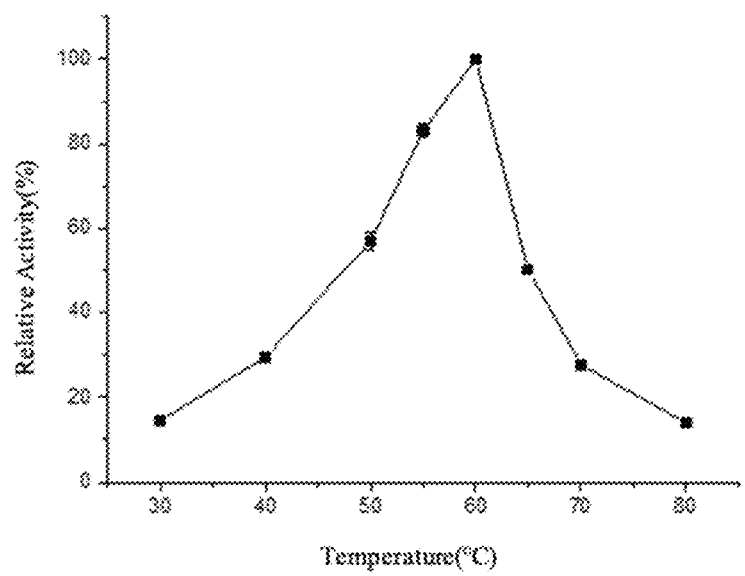
FIG. 5 shows the optimal temperature of β-glucosidase TpBgl3A.

3. Enzymatic Properties of β-Glucosidase (1) Optimal Temperature of β-Glucosidase The enzymatic properties were determined for the enzyme solution of β-glucosidase obtained by the above fermentation. The enzyme activity was measured at different temperatures with pNPG as the substrate. The results showed that the relative enzyme activities of β-glucosidase at 50° C. and 65° C. were 57.04% and 50.08%, respectively, and the optimal temperature was 60° C. (FIG. 5).

(2) Optimal pH of β-Glucosidase

Figure 6:
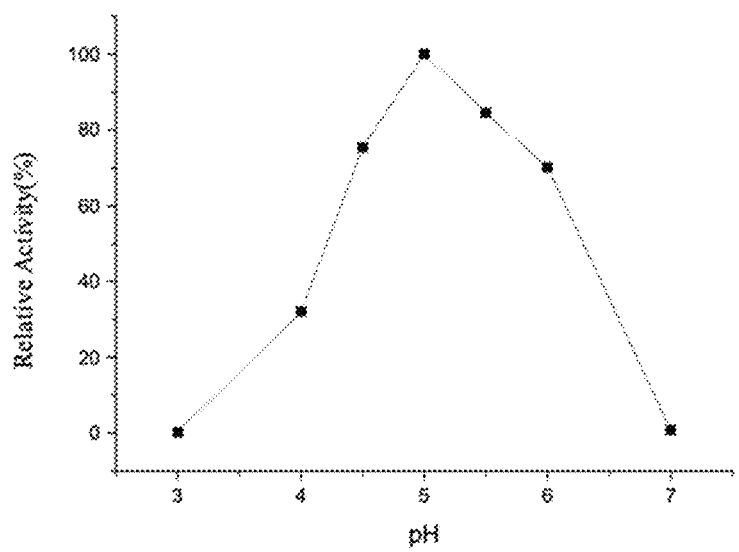
FIG. 6 shows the optimal pH value of β-glucosidase TpBgl3A.

The enzyme activity of β-glucosidase was measured with different pH gradients at the optimal temperature of 60° C. The results showed that the relative enzyme activities of β-glucosidase at pH 4.5, 5.5, and 6.0 were 75.49%, 84.51%, and 70.22%, respectively, and the optimal pH was 5.0 (FIG. 6).

Figure 7:
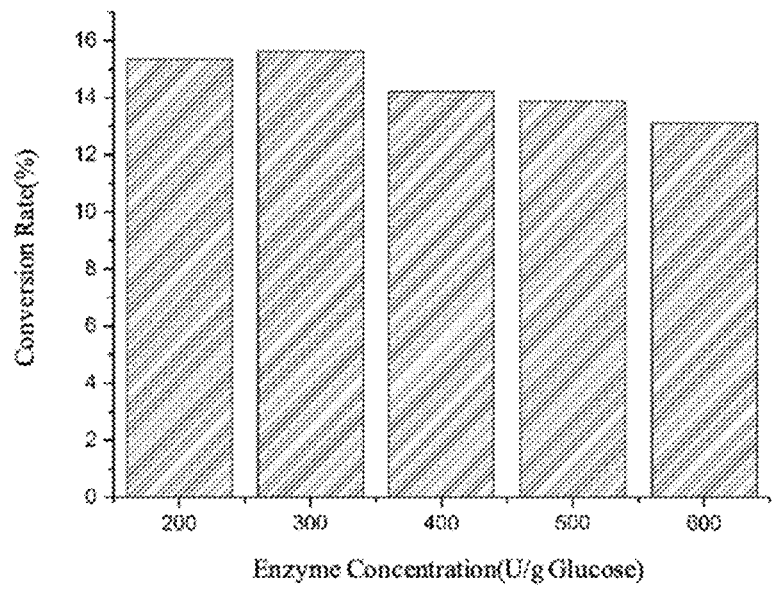
FIG. 7 is a diagram showing the relationship between the enzyme amount of β-glucosidase TpBgl3A added and the conversion rate for preparing gentioligosaccharides with glucose as a substrate.

Example 3: Application of β-Glucosidase in the Preparation of Gentioligosaccharides with Glucose as a Substrate The reaction system for preparing gentioligosaccharides with glycose as a substrate: the reaction was carried out at pH 5.0 and 60° C. for 72 h with 800 g/L glucose as a substrate, and the influence of different enzyme amounts of β-glucosidase added (200-600 U/g glucose) on the enzyme reaction was explored. The results are shown in FIG. 7. The cumulative content of gentioligosaccharide increased with the increase of the enzyme amounts added within a certain range. However, when the enzyme amount added was more than 300 U/g glucose, increasing the enzyme amount added would reduce the production of gentioligosaccharide. Therefore, it is most suitable to choose the enzyme amount added of 300 U/g glucose. At this time, the yield of gentioligosaccharide can reach 125.0 g/L, and the conversion rate was 15.62%.

Formula for calculating conversion rate:

$$\text{yield}(\%) = \frac{\text{mass of the gentioligosaccharide in the product}}{\text{mass of all sugars in the product}} \times 100\%$$

TABLE 4

Yield and conversion rate for preparing gentioligosaccharides
with glucose as a substrate under different enzyme amounts added

| Enzyme amount added (U/g glucose) | 200 | 300 | 400 | 500 | 600 |
|---|---|---|---|---|---|
| Yield of gentioligosaccharide (g/L) | 122.7 | 125.0 | 113.7 | 109.0 | 106.5 |
| Conversion rate of gentioligosaccharide, % | 15.33 | 15.62 | 14.21 | 13.63 | 13.31 |

Comparative Example 1

Comparative example 1 was carried out in the same manner as in Example 3, except that the β-glucosidase was replaced with the β-glucosidase derived from *Trichoderma viride*. The enzyme amount added was set to 300 U/g glucose, and the yield and conversion rate of gentioligosaccharide were determined as 60 g/L and 7.5%, respectively.

On this basis, under the optimal condition for the enzyme conversion of β-glucosidase derived from *Trichoderma viride* where the reaction was carried out at pH 5.0, 60° C., the enzyme amount added was 900 U/g glucose, and the concentration of glucose as substrate was 800 g/L, the yield of gentioligosaccharide can reach the maximum value of 130 g/L, the conversion rate was 16.25%, and the high-density fermentation level was 1402 U/mL.

Figure 8:
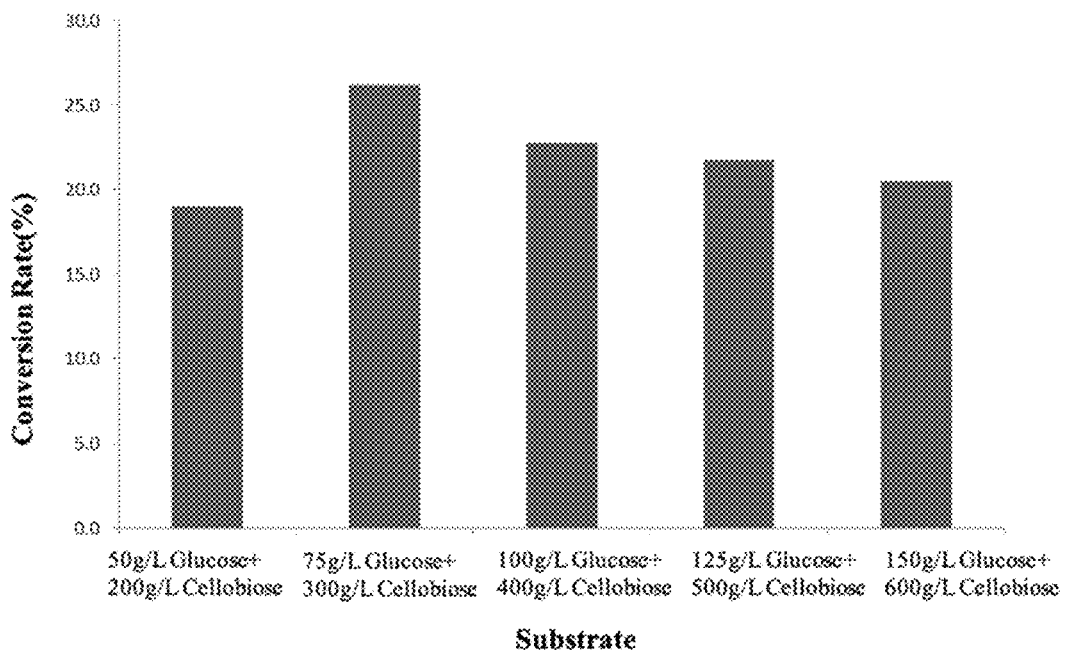
FIG. 8 is a diagram showing the relationship between the substrate concentration and the conversion rate for preparing gentioligosaccharides with glucose and cellobiose as the substrate.

Example 4: Application of β-Glucosidase in the Preparation of Gentioligosaccharides with Glucose and Cellobiose as Substrates The reaction system for preparing gentioligosaccharides with glucose and cellobiose as substrates: the reaction was carried out at pH 5.0 and 60° C. for 48 h when the molar concentration ratio of glucose to cellobiose was maintained at 1:2 (mass concentration ratio of 1:4), 50-150 g/L glucose and 200-600 g/L cellobiose were used as the substrates, and the enzyme amount added was 400 U/g cellobiose. The results showed that the optimal substrate concentration was 75 g/L glucose and 300 g/L cellobiose, and the highest conversion rate of gentioligosaccharide was 26.2% (FIG. 8).

TABLE 5

The yield and conversion rate for preparing gentioligosaccharides with
glucose and cellobiose as substrates at different substrate concentrations

| Substrate concentration | 50 g/L glucose + 200 g/L cellobiose | 75 g/L glucose + 300 g/L cellobiose | 100 g/L glucose + 400 g/L cellobiose | 125 g/L glucose + 500 g/L cellobiose | 150 g/L glucose + 600 g/L cellobiose |
|---|---|---|---|---|---|
| Yield of gentioligo-saccharide (g/L) | 47.6 | 98.2 | 113.7 | 81.6 | 153.8 |
| Conversion rate of gentioligo-saccharide, % | 19.0 | 26.2 | 22.7 | 21.7 | 20.5 |

Comparative Example 2

Comparative example 2 was carried out in the same manner as in Example 4, except that the β-glucosidase was replaced with the β-glucosidase derived from *Trichoderma viride*. Under the optimal condition for enzyme conversion where the reaction was carried out at pH 5.0, 60° C., the substrate concentration was 20% glucose and 40% cellobiose, and the enzyme amount added of β-glucosidase was 400 U/g cellobiose, the conversion rate of gentioligosaccharide was 19.4%.

Although the present disclosure has been disclosed as above in preferred examples, it is not intended to limit the present disclosure. Those skilled in the art can make various modifications and changes without departing from the spirit and scope of the present disclosure. Therefore, the protection scope of the present disclosure should be defined by the claims.

What is claimed is:

1. A method for producing gentiooligosaccharide, comprising producing gentiooligosaccharide with glucose or a combination of glucose and cellobiose as a substrate using β-glucosidase expressed by a recombinant bacteria carrying a gene with the nucleotide sequence as set forth in SEQ ID NO:1.

2. The method according to claim 1, wherein the amino acid sequence of the β-glucosidase is as set forth in SEQ ID NO:2.

3. The method according to claim 2, wherein when glucose is used as the substrate, a concentration of glucose is 800 g/L.

4. The method according to claim 3, wherein an amount of enzyme β-glucosidase added is 200-300 U/g glucose.

5. The method according to claim 3, wherein a reaction is carried out at pH 5.0 and 60° C. for not less than 72 h.

6. The method according to claim 2, wherein when a combination of glucose and cellobiose is used as the substrate, a concentration of glucose is 75 g/L and a concentration of cellobiose is 300 g/L; or, a concentration of glucose is 100 g/L and a concentration of cellobiose is 400 g/L.

7. The method of claim 6, wherein an amount of the β-glucosidase added is 400 U/g cellobiose.

8. The method according to claim 6, wherein a reaction is carried out at pH 5.0 and 60° C. for 48 h.

* * * * *